United States Patent
Hurst et al.

(10) Patent No.: US 6,208,942 B1
(45) Date of Patent: *Mar. 27, 2001

(54) MOLECULAR HOLOGRAM QSAR

(75) Inventors: John Robert Hurst, San Diego, CA (US); Trevor William Heritage, O'Fallon, MO (US)

(73) Assignee: Tripos, Inc, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/022,252

(22) Filed: Feb. 10, 1998

Related U.S. Application Data

(63) Continuation-in-part of application No. 08/698,040, filed on Aug. 15, 1996, now Pat. No. 5,751,605.

(51) Int. Cl.[7] .................................................. G06F 19/00
(52) U.S. Cl. .............................. 702/27; 702/31; 700/268; 700/293
(58) Field of Search ................................ 702/27, 30, 31; 700/268, 293

(56) References Cited

U.S. PATENT DOCUMENTS

| | | | |
|---|---|---|---|
| 5,025,388 | * | 6/1991 | Cramer, III et al. ............... 700/293 |
| 5,418,944 | * | 5/1995 | DiPace et al. ...................... 702/27 |
| 5,463,564 | * | 10/1995 | Agrafiotis et al. ................. 702/31 |
| 5,751,605 | * | 5/1998 | Hurst et al. ........................ 702/27 |

* cited by examiner

*Primary Examiner*—Patrick Assouad
*Assistant Examiner*—Bryan Bui
(74) *Attorney, Agent, or Firm*—Laurence A. Weinberger

(57) ABSTRACT

A new computer implemented method for discovering structure-activity relationships has been discovered which utilizes weighted 2D fingerprints in conjunction with the PLS statistical methodology. This method produces a robust QSAR technique that can be automated. In addition, the MOLECULAR HOLOGRAM QSAR technique generates high quality QSAR models that are in many cases as good as or better than models arising from use of more complex and time consuming techniques such as CoMFA or Apex-3D.

19 Claims, 9 Drawing Sheets

| | OBSERVED BIOLOGICAL PARAMETER | VALUES OF MOLECULAR DESCRIPTORS USED | | | | | | |
|---|---|---|---|---|---|---|---|---|
| MOL. 1 | $Ob_1$ | A1 | B1 | C1 | D1 | E1 | F1 | ... | (n)1 |
| MOL. 2 | $Ob_2$ | A2 | B2 | C2 | D2 | E2 | F2 | ... | (n)2 |
| MOL. 3 | $Ob_3$ | A3 | B3 | C3 | D3 | E3 | F3 | ... | (n)3 |
| MOL. 4 | $Ob_4$ | A4 | B4 | C4 | D4 | E4 | F4 | ... | (n)4 |
| MOL. 5 | $Ob_5$ | A5 | B5 | C5 | D5 | E5 | F5 | ... | (n)5 |
| ... | | | | | | | | | |

MOLECULAR HOLOGRAM QSAR

This application is a continuation-in-part of U.S. application serial No. 08/698,040 filed Aug. 15, 1996, now U.S. Pat. No. 5,751,605, for which a Notice of Allowability was issued on Sep. 24, 1997.

BACKGROUND OF THE INVENTION

1. Field of the Invention

This invention relates to the field of chemical discovery and to understanding the relationship between the structure of a molecule and its chemical function (a structure/function relationship) and especially as structure/function relationships relate to biological chemical discovery in the search for new medicinal drugs. In particular, a method has been discovered that uses an iterative process of determining, using the partial least squares method of multivariate analysis, which definition of a specialized 2D fragment molecular metric best characterizes the structure-activity relationship among a series of molecules having similar activities. Once identified, this definition can be used to visualize, in a computer graphics environment, the relative contributions of each portion of a molecule to its chemical activity.

2. Description of Related Art

1. Structure-Activity Relationships

In the never-ending search for new and more effective drugs with which to treat disease, one approach to discovery has been the mass screening of naturally occurring chemical compounds. More recently, huge schemes of combinatorial chemical synthesis have produced mass numbers of additional chemical compounds available for screening. However, once an active chemical is identified, a search must still be conducted to find the molecular relative of the identified molecule which has the greatest activity in the desired biological system. One of the principal techniques employed by medicinal chemists has been to examine the chemical structures of a series of molecules which are related by the fact that they all exhibit some activity in the biological system of interest, and, relying on fundamental chemical and physical principles, making educated guesses as to which part or parts of the molecules is/are most important to the activity. Based on these guesses, new compounds can be synthesized and tested.

Over the years quantitative approaches to relating structure and activity were developed to supplant the intuitive guess of chemists. These approaches generally sought to cast the observed/measured biological value (Ob) in terms of a linear combination of molecular descriptors A, B, C, etc. [Ob=A+B+C ... (n)] Thus, for each of the molecules which are related by the fact that they all exhibit some activity in the biological system of interest, a row is entered in a data table (matrix) for that molecule as shown in FIG. 1. Unless (which was rarely, if ever, the case) the number of molecules equaled the number of descriptor values, an inherently underdefined system of equations was presented, and no explicit solution could be found. Various molecular descriptors were developed to characterize the molecules having similar activities and a relationship was sought by applying various statistical methods of analysis (such as multiple linear regression) to the underdetermined data table.

These systems of "quantitative structure activity relationships" (acronymed QSAR) enjoyed modest success in drug design but generally failed in their attempt to quantitatively take the three dimensional shape of molecules into account, a necessary requirement for biological systems for which the three-dimensional stereo conformation of biomolecules and their substrates has been shown to be of preeminent importance. Ultimately in 1988, a sophisticated method (CoMFA[1]) of comparing the three-dimensional shapes of molecules and relating the shapes to observed biological activity differences to identify the most important common topological features of the molecules was developed. Typically, molecular shape descriptors consisting of thousands of terms were defined for a relatively few molecules. The resulting data table was successfully analyzed using the Partial Least Squares (PLS) statistical technique to extract meaningful structure-activity information. This Comparative Molecular Field Analysis (CoMFA) approach has been remarkedly successful and has enjoyed wide acceptance and usage. However, to use CoMFA, skilled medicinal-computational chemists are required to make difficult and complex decisions regarding molecular conformation and relative alignment and a significant amount of computational time is then required to achieve the full benefits of COMFA.

2. 2D Molecular Fingerprints

Molecular fingerprints are bitmaps representative of a molecule and have been primarily used to efficiently search databases and to analyze chemical similarity[2]. Essentially, a long binary bit string which consists of 0s and 1s is created for each molecule. Each position along the string is assigned to a specific molecular fragment. If that fragment exists in the molecule under consideration, the corresponding bit is set to 1, otherwise it is left as a 0. For the present purposes, two interwoven characteristics of the bit strings are important. First, because of the way in which fragments are defined, the same molecular structure (functional group, atomic arrangement, etc.) may be included in more than one fragment and, thus, contribute to setting more than one bit in the string at 1. As a result of this, more than one unique molecule may specify the same bit string. Put another way, there is an inherent degeneracy in this method so that one can not go backwards to a molecule from a knowledge of its bitmap. Further, despite the fact that fragments must have some relationship to the three dimensional structure of the molecule, that relationship is not explicitly incorporated in the bitmap. Thus, it is generally acknowledged that no information relating to the three dimensional structure is directly encoded is this type of bitmap, and it is, accordingly, referred to as a 2 Dimensional (2D) representation.

Similarity assessments between molecules based on 2D fingerprints are most commonly performed using the Tanimoto coefficient[2], which compares the number of fingerprint bits in common between pairs of structures. Most recently, a technique has been developed which identifies structural commonalities in sets of compounds[3]. This technique (known as Stigmata) essentially ANDs (in a Boolean sense) the 2D fingerprints (binary bit strings) of the structures in the data set and identifies fingerprint bits held in common across some percentage of the data set.

There are two general methods of 2D fingerprint generation supplied by the companies which develop and promote them. The first, known as the keyed[4] method, and a second known as the hashed[5] method. The keyed method requires a priori substructural definitions for all the fragments that should be searched for during the fingerprint generation process; if a fragment is not specified in the input list, it will not be included in the fingerprint. The hashed method uses a set of rules for generating fragments for fingerprinting. That is; generic rules are applied that define how a chemical structure should be broken down into constituent fragments. The hashed method uses these rules to generate all possible unbranched fragments. Both methods result in a binary bit string (0s or 1s) that encode the presence or absence of particular fragments.

In the past, attempts to use 2D FINGERPRINTS to generate useful QSARs have not been successful no matter what type of correlation scheme was employed. It is believed that this was the case because an insufficient amount of three-dimensional information about the molecules was contained in the essentially two-dimensional fingerprint.

Definitions

2D FINGERPRINTS shall mean a 2D molecular measure in which a bit in a data string is set corresponding to the occurrence of a given length atom fragment in that molecule. Typically, strings of roughly 900 to 2400 bits are used depending on how many different combinations of components are utilized. A particular bit may be set by many different fragments.

MOLECULAR HOLOGRAM shall mean a weighted 2D FINGERPRINT in which all possible fragments are counted with each position in the fingerprint to which each fragment is assigned being weighted by the frequency of each fragment's occurrence in the molecule. In the case where more than one fragment is assigned to the same position in the fingerprint (as in a hashed fingerprint), the position in the fingerprint will be additionally weighted by the frequency of occurrence of all fragments assigned to that position.

SUMMARY OF THE INVENTION

A new method of quantitatively relating the structure of a drug to its function has been discovered which should significantly speed up the process of drug design and identification. The method of the present invention relies upon the characterization of molecular structures by a new approach to molecular fragment analysis and a subsequent analysis across the defined fragments by an iterative process using Partial Least Squares methodology. Rather than restricting the fragment analysis to either an arbitrary initial set (keyed method) or all fragments of a predetermined size (hashed method), a MOLECULAR HOLOGRAM is defined for a given molecule by generating all chosen fragments including branched and cyclic ones with between M and N atoms. In addition, a count is maintained of the number of times each fragment is encountered in a molecule. Thus, a string of integers rather than a bitstring of 0s or 1s is generated for each molecule. The string of integers is reduced in length by hashing to a variable length running up to length L. For a given data set of molecules, all possible combinations of M, N, and L are calculated and the data table corresponding to each combination is analyzed by Partial Least Squares Analysis. The relative values of the cross validated $r^2$ are used to identify the optimum QSAR.

The values of M, N, and L corresponding to the optimal QSAR can be used to quickly scan (by computing the Molecular Hologram) a data base of molecules for those compounds which are most likely to have the same biological activity as the compounds in the data set from which the HQSAR was derived. In addition, the HQSAR weighting resulting from the PLS analysis can be used to graphically indicate which atoms in each of the data set molecules contributed positively or negatively to the successful correlation with the biological data.

DESCRIPTION OF FIGURES

FIG. 1 shows a typical QSAR data table in which each row corresponds to information relating to a single compound and each column corresponds to a parameter value used to characterize the compounds.

DETAILED DESCRIPTION OF THE INVENTION

1. Computational Chemistry Environment

Figure 2:
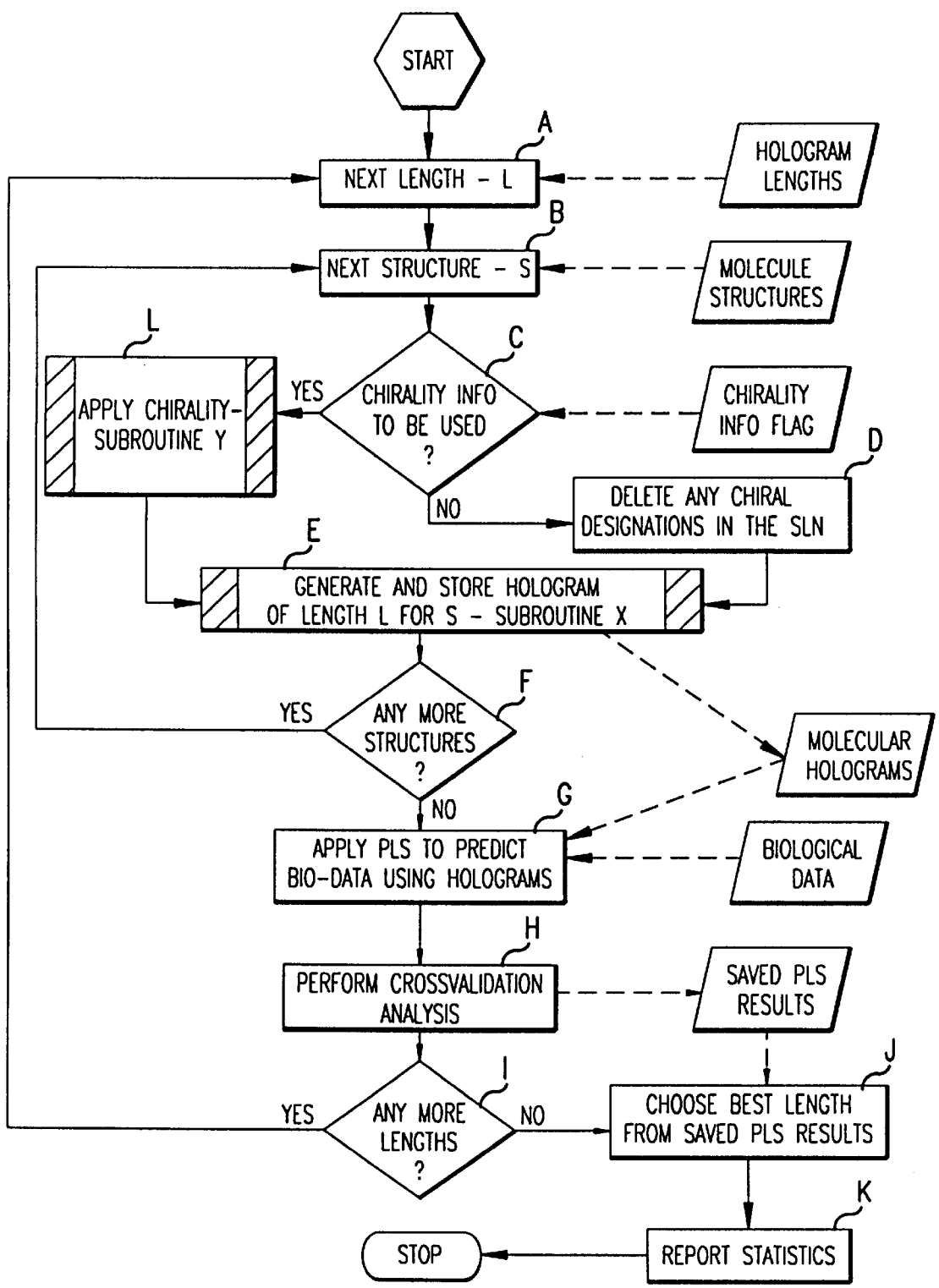
FIG. 2 is a flowchart showing the overall process of the invention.

Generally, all calculations and analyses to derive structure-activity relationships are implemented in a modern computational chemistry environment using software designed to handle molecular structures and associated properties and operations. For purposes of this Application, such an environment is specifically referenced. In particular, the computational environment and capabilities of the SYBYL and UNITY software programs developed and marketed by Tripos, Inc. (St. Louis, Mo.) are specifically utilized. Unless otherwise noted, all software references in the following text are references to functionalities contained in the SYBYL and/or UNITY software programs. Software with similar functionalities to SYBYL and UNITY are available from other sources, both commercial and non-commercial, well known to those in the art. A general purpose programmable digital computer with ample amounts of memory and hard disk storage is required for the implementation of this invention. In performing the methods of this invention, representations of molecules and/or molecular structures as well as other data may need to be stored simultaneously in the random access memory of the computer or in rapidly available permanent storage. The inventors use a Silicon Graphics, Inc. Indigo computer having a single 150 Mhz R4400 processor with 128 Mb memory and 4 Gb hard disk storage space.

2. Outline of the Invention

This invention arises from the discovery that several different processes of molecular analysis when uniquely combined unexpectedly yield valid quantitative structure-activity relationships reflective of three dimensional molecular interactions using what has been traditionally viewed as two-dimensional data, namely 2D fingerprint fragments. The individual processes are:

a. constructing a list of all possible molecular fragments including branched and cyclic fragments;

b. using the fragment list to generate a MOLECULAR HOLOGRAM of variable length;

c. analyzing the data tables composed of the MOLECULAR HOLOGRAMS for each molecule in the data set and their associated activities with PLS by consecutively preforming PLS on each of the data tables associated with each length to determine which fragment pattern and hashed length best reflects the structure-activity relationships of the data set;

d. using the PLS solution coefficients of each fingerprint position derived from the optimally selected structure-activity relationship to visualize which atoms of each molecule contribute positively or negatively to the observed structure-activity relationship.

Each of these general processes will be discussed in order below.

3. Derivation of the Molecular Hologram

MOLECULAR HOLOGRAM generation occurs in a fashion analogous to the hashed method of 2D fingerprint generation except for two critical differences. First, all possible fragments are generated, including the branched and cyclic ones. This assures that all fragments which may be involved in the three-dimensional chemical interactions in which the molecule participates are included. A MOLECULAR HOLOGRAM is defined for a given molecule by generating all possible combinations of fragments with between M and N atoms. These values are specified as input variables by the user of the HQSAR methodology. In typical applications, values of M used start as low as two and values of N used range to 12. Clearly, however, N may range up to a maximum value equal to the number of atoms in the molecule. When Sybyl is used, the fragments are described using Sybyl Line Notation (SLN), although they could equally well be described using any other connection table format. Such formats are standard and are well known to those in the art.

The second key difference between prior art 2D fingerprints and the MOLECULAR HOLOGRAM is that the MOLECULAR HOLOGRAM actually maintains a count of all of the times a fragment associated with a given fingerprint position is encountered, and the resulting hologram is a string of integers representing these counts. Thus, where a standard 2D fingerprint might be of the form:

1 1 0 1 0 1 1 1 0 1 0 1 1 1 1 . . .

a MOLECULAR HOLOGRAM might appears as:

2 1 4 5 124 5 7 3 11340 7 . . .

While standard 2D fingerprints do not produce useful QSARs, the combination of these MOLECULAR HOLOGRAMS with the other aspects of the present invention discussed below has yielded very significant results.

During MOLECULAR HOLOGRAM generation, the following features of fragments can optionally be taken into account during the generation of fragments:

atomic (elemental) types bond types atomic connectivity information (equivalent to hybridization of atoms)

hydrogen atoms may be included or ignored atomic stereochemistry (chirality) and bond stereochemistry may either be included or ignored The inclusion of stereochemistry within the MOLECULAR HOLOGRAM is a unique feature that has not been used in other fingerprinting techniques. This feature makes use of stereochemical assignments on the input chemical structure, such as those defined with stereo SLNs, and distinguishes between enantiomers and E/Z isomers.

3. Hashing to defined lengths.

Standard 2D bitstring fingerprints can be fairly long, as noted above, and MOLECULAR HOLOGRAMS which encompass all possible fragments are even longer. In addition, over a set of molecules, many of the fingerprint terms will contain 0s; that is, have no useful information content. For subsequent computation of the PLS for a data set, the time of computation is dramatically increased as the length of the fingerprint goes up, and is further hindered by the presence of null values. Thus, some method must be used to reduce the length of the fingerprints. This reduction is achieved by assigning many fragments to the same location in the fingerprint—a process referred to as "hashing". Consider the following examples:

BY_LENGTH 1–85 4–6 NO_HYDROGENS

The above definition means generate all possible fragments (including overlapping fragments) that are of length 4 to 6 atoms, ignoring hydrogen atoms, and hash them to positions 1 to 85 in the fingerprint.

BY_SLN5–11 sln=Any[1]~Any~Any~Any~Any~Any~@1 NO. NO_DUPLICATES

The above definition means: identify all rings containing six atoms, ignoring duplicate ring systems, and hash them to positions 5 to 11 in the fingerprint.

The "hashing" process specified above is required since, as in the first example, more than 85 unique fragments will be generated while only 85 positions (bins) have been specified for the fingerprint. The "hashing" process uses a standard procedure (cyclic redundancy check [CRC]) to convert a text string representing a fragment (in this case a SYBYL Line Notation, SLN, representation of chemical structure) into a pseudo-random very large integer that is reproducible and always associated with that particular fragment. This number is then folded into the allotted number of fingerprint positions or bins (85 in this example).

In the process of this invention, the fragments are hashed into the range 1 through L, where L represents the length of the MOLECULAR HOLOGRAM and is an input parameter supplied by the user of the HQSAR methodology. Each time a given fragment is encountered in the molecule, the corresponding hologram bin is incremented.

The hologram length may either be pre-set, in which case different fragments may hash to the same bin (hashed hologram), or the hologram length can be calculated on-the-fly to ensure that one and only one type of fragment contributes to each bin (specific hologram). Two other types of molecular hologram have been investigated—the extended hologram and the keyed hologram. The Extended Hologram is used to indicate only the presence of a fragment in the molecule 1 through k times, rather than counting the total number of times each unique fragment occurs. This type of hologram is generated by sub-dividing each bin from the Hashed Hologram into k sub-bins. The Keyed Hologram is based on the Specific Hologram, but counts only fragments which match some sub-structural pattern. Of the hologram types, the hashed hologram has been found to be most useful for the generation of meaningful HQSARs.

Once the hashed MOLECULAR HOLOGRAM has been determined for each molecule in a given series, a data table as shown in FIG. 1 is constructed. Each row is now made up of the observed value and the associated hashed hologram for that molecule. It should be noted that any property associated with or used to describe a molecule can be used to generate a QSAR by the method of this invention as long as the same type of property is used for every molecule in the data set. Biological and chemical activities and physical properties are good examples.

4. Generation of HOSARs.

Unlike previous attempts to find useful QSARs by employing conventional 2D FINGERPRINTS, it has been discovered that the application of either partial least squares (PLS) or classification analysis to MOLECULAR HOLOGRAMS leads to surprisingly high quality quantitative models relating molecular structure to observed activity (QSAR) across a broad range of activities and molecular structures. PLS is now a well recognized technique for QSAR derivation in the prior art. For instance, a discussion of PLS and the method of leave-one-out cross validation as applied to QSAR derivation appears in Cramer's U.S. Pat. No. 5,025,388 and European Patent No. 0592421 both for CoMFA. The range of activities and molecular structures in the data sets studied with HQSAR included sulfonamide endothelin-A antagonists, anticoccidial triazines, σ1 binding benzyl-N-normetazocines, benzodiazepines, corticosteroids, hydrazide MAO inhibitors, benzindole $5HT_{1a}$ antagonists, and ryanodine analogs. In most cases examined, the methodology of this invention (using the hashed hologram) allowed successful derivation of QSAR models comparable or better than those obtained in equivalent studies using traditional molecular descriptors (cLogP/cMR), connectivity indices, or Comparative Molecular Field Analysis (CoMFA).

Advantages of the MOLECULAR HOLOGRAM are that it is simple and rapid to calculate, and it can be readily understood and applied by medicinal chemists to problems of interest. Although the molecular descriptions are derived from 2D information only, the QSAR results are as good as those obtained using the leading 3D QSAR techniques. It is for this reason that these fingerprints are called MOLECULAR HOLOGRAMS since they reflect three-dimensional structures just as a two-dimensional optical hologram contains information about three-dimensional structures. These properties of MOLECULAR HOLOGRAMS render them suitable for application in many areas of pharmaceutical discovery, such as QSAR, database searching and lead prioritization.

As indicated above there are three parameters (M, N, and L) which control exactly how the MOLECULAR HOLOGRAM is built. In the method of this invention, no rigid definition of fragment or hologram length is set. Rather, as part of the HQSAR generation process, fragments of all different lengths are used and hashed into holograms of different lengths. A full PLS analysis is then run on every single chosen combination of fragment sizes and hologram lengths (all such combinations being applied to all molecules in the data set) to determine the combination of parameters (M, N, and L) which yields the optimum HQSAR. The advantage of this approach lies in the fact that there is no a priori way of telling which pattern of fragment disposition and hologram length can best be analyzed by PLS to detect the relationship between fragments present in the data set and the observed activities.

Calculation of the MOLECULAR HOLOGRAMS for a data set of molecular structures to be used in a QSAR analysis generates a data matrix as shown in FIG. 1 of dimensions R x L, where R is the number of compounds in the data set (rows) and L is the length of the MOLECULAR HOLOGRAM (columns). Values (observed/measured/calculated) associated with each molecule are also entered into the matrix as an additional column. Standard PLS analysis[6] is then applied to identify a set of orthogonal explanatory variables (components) that are linear combinations of the original L variables. The statistical cross-validation technique is used to determine the number of components that yields an optimally predictive model.

Once an optimal model is identified, PLS yields a model that relates the MOLECULAR HOLOGRAM bin values to the biological activity. The equation takes the following form:

$$\text{Predicted Activity} = \sum_{i=1}^{L} X_i C_i + \text{Const.}$$

where $X_i$ is the integer value of the MOLECULAR HOLOGRAM of the compound to be predicted at position i (or bin i), and $C_i$ is the coefficient for that position (or bin) derived from the PLS analysis.

The process of HQSAR model derivation requires identification of those parameters (M, N, and L) which lead to an optimal QSAR model. The process of this invention is outlined in the flowcharts of FIGS. 2, 3, 4, 5, 6, 7, and 8. Each flowchart will be briefly discussed highlighting the important features.

FIG. 2 is a summary flowchart of the process of the invention. As is customary in flowchart presentation, the parallelogram boxes on the right indicate data input and output during the process. Letter references are to steps indicated in the flowcharts. The basic cyclic outline of the method of this invention can be clearly seen. For each length L, all molecules in a data set are broken down into their constituent fragments and MOLECULAR HOLOGRAMs generated for each molecule. The resulting set of MOLECULAR HOLOGRAMS is associated with the related biological data and is analyzed with PLS and the results stored. The next length L is then considered and the process repeated. When all lengths L have been used, the PLS results are compared to determine the optimal structure-activity relationship determined and the length L and the related values of M and N are reported.

More specifically, as can be seen in FIG. 2, the process starts at "A" with the specification of a first length L for which a HQSAR will be calculated. At "B" the first molecule is specified. Whether to use chiral information is tested at "C", and if chiral information is to be used Subroutine Y is called at "L". Subroutine Y is discussed with FIGS. 5 and 6. The ability to take chiral information into account when creating the MOLECULAR HOLOGRAM is a significant feature of this invention. If chiral information is to be used, the chiral SLNs are returned by Subroutine Y and a MOLECULAR HOLOGRAM for all fragments found is generated by Subroutine X at "E" and is stored. If chiral information is not to be used, any chiral information already present in the SLNs is deleted at "D" before the MOLECULAR HOLOGRAMS are generated at "E". Values of M and N supplied by the user are used for this generation. Generation of the MOLECULAR HOLOGRAMS will be detailed in the discussion of FIG. 3 below. A check is made at "F" to determine whether any more holograms need to be calculated for additional molecules, and, if there are, the process loops back to "B" and is repeated. This loop is repeated for all molecules. At "G" the MOLECULAR HOLOGRAMS are associated with the biological data and a Partial Least Squares analysis is applied with a cross-validation analysis at "H" and the results are stored. Thus, for each length L, both a cross-validated $r^2$ and a standard error of prediction are calculated both of which are reflective of the ability of the MOLECULAR HOLOGRAMS of that length to predict the actual data. At "I" a check is performed to determine whether any more hologram lengths are to be considered, and, if there are, the process loops back to "A" and is repeated. If there are no more lengths to be considered, at "J" the hologram length and the associated values of M and N which produced the smallest standard error are chosen as the optimal HQSAR and reported at "K".

Figure 3:
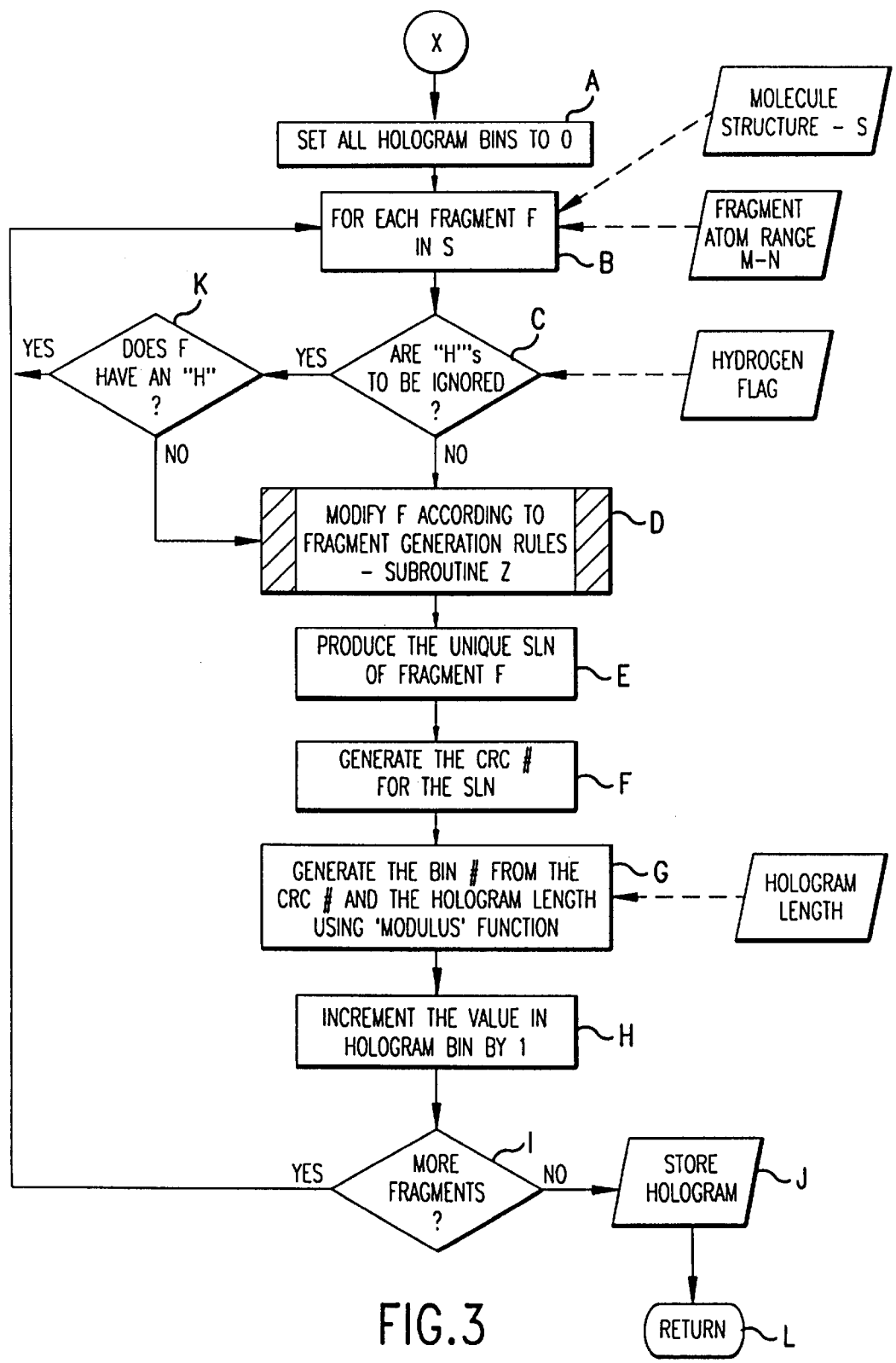
FIG. 3 is a flowchart showing the MOLECULAR HOLOGRAM generating process.

Subroutine X shown in the flowchart of FIG. 3 generates the MOLECULAR HOLOGRAMS for each length L. The cyclic nature of the fragment generating process is clearly seen. For each fragment of a size determined by the values of M and N a unique fragment description (SLN) is determined which is used to generate a pseudo-random number. Using the modulus operator with the pseudo-random number and the length L, a bin or position in hologram is determined which should have its value incremented for the occurrence of that fragment.

More specifically, as can be seen in FIG. 3, initially all bin (position) values are set to zero at "A" and an initial fragment specified at "B" within the size range M to N specified by the user. A check is performed at "C" to determine whether hydrogen atoms are to be taken into account or ignored. If hydrogens are to be ignored, the test at "K" determines if the fragment contains hydrogen. If the fragment contains hydrogen, the process loops back to the next fragment at "B". The atoms making up such a hydrogen containing fragment will ultimately be included in another fragment of shorter length. If hydrogens are not to be ignored or if the fragment does not have any hydrogens the process continues at "D" with fragment modification according to certain rules in Subroutine Z. Subroutine Z is discussed with FIG. 4. For each fragment a unique SLN fragment description is generated at "E". Based upon the SLN fragment description, at "F" a cyclic redundancy check number is generated for the fragment defined by the SLN. This number is a pseudo-random number which will always be generated for the specific fragment defined by the SLN. The position in the fingerprint which will be assigned to this fragment is generated from the CRC number and the hologram length L using the standard mathematical operator "modulus" at "G". In this manner a long fingerprint is folded or hashed into a shorter length. Clearly, as the process loops, several fragments may be assigned to the same position or bin in the fingerprint. For the fragment under consideration at "G", the value in the specified bin is incremented by the value 1 at "H". Thus, for every occurrence of a particular molecular fragment, the same bin or position will be incremented. The bin will also be incremented by other fragments which are assigned to it. At "I" a check is performed to determine whether there are any more fragments to consider, and, if there are, the process loops back to "B". If there are no more fragments to consider for the molecule, the hologram is stored at "J" and the subroutine returns at "L".

Figure 4:
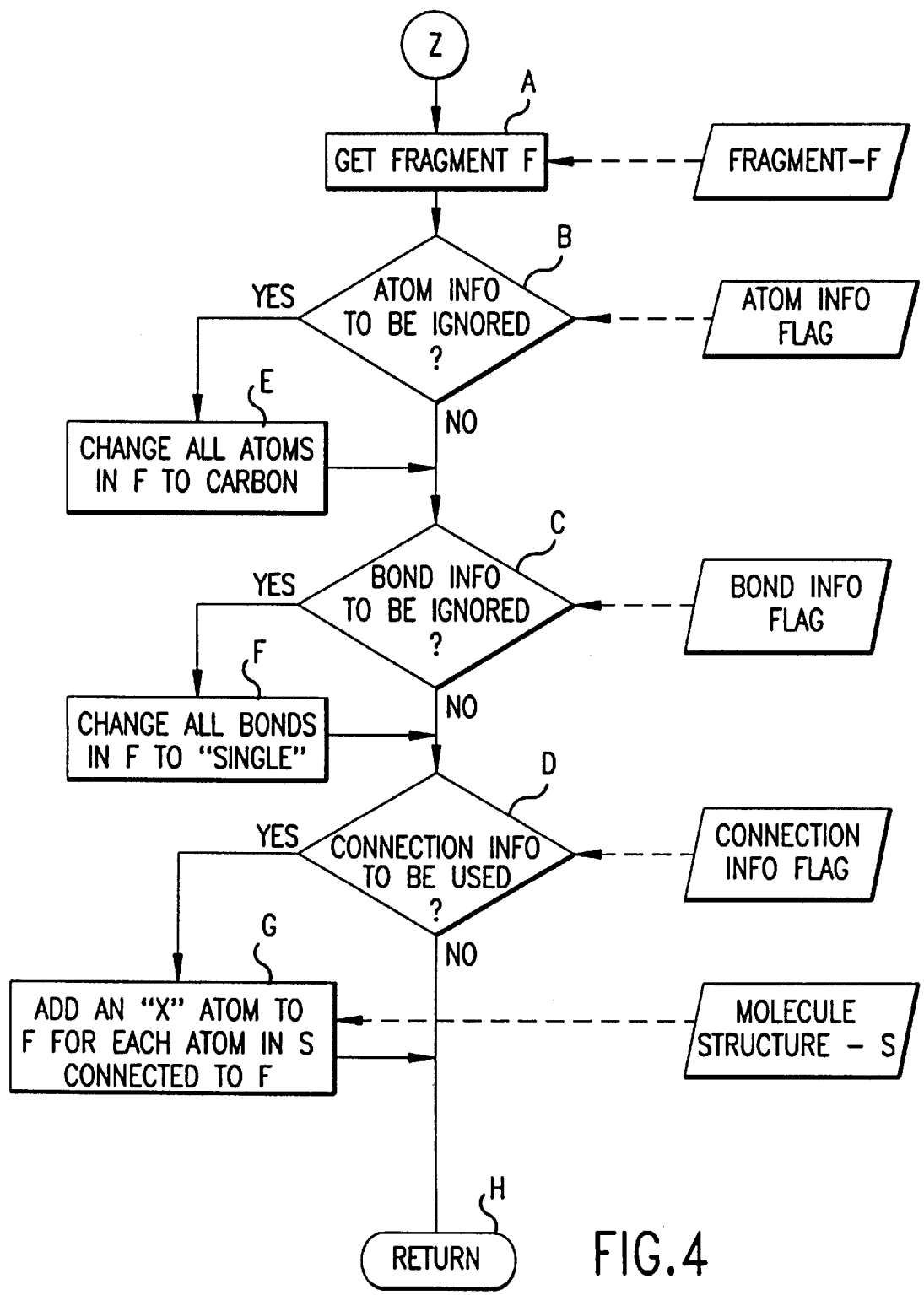
FIG. 4 is a flowchart showing part of the fragmentation generating process.
Figure 5:
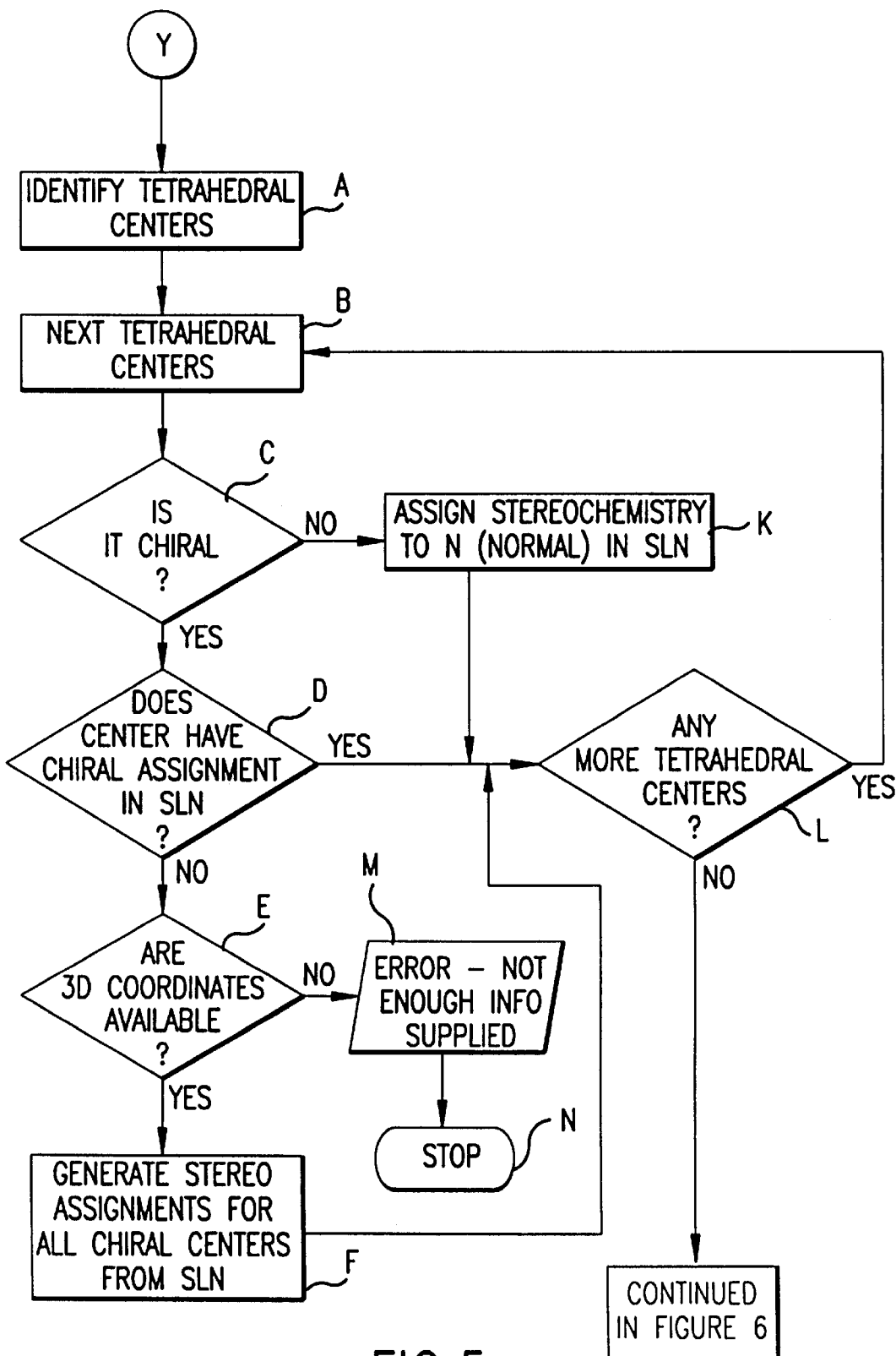
FIGS. 5 and 6 are a flowchart showing how chirality is incorporated into the MOLECULAR HOLOGRAM generating process.
Figure 6:
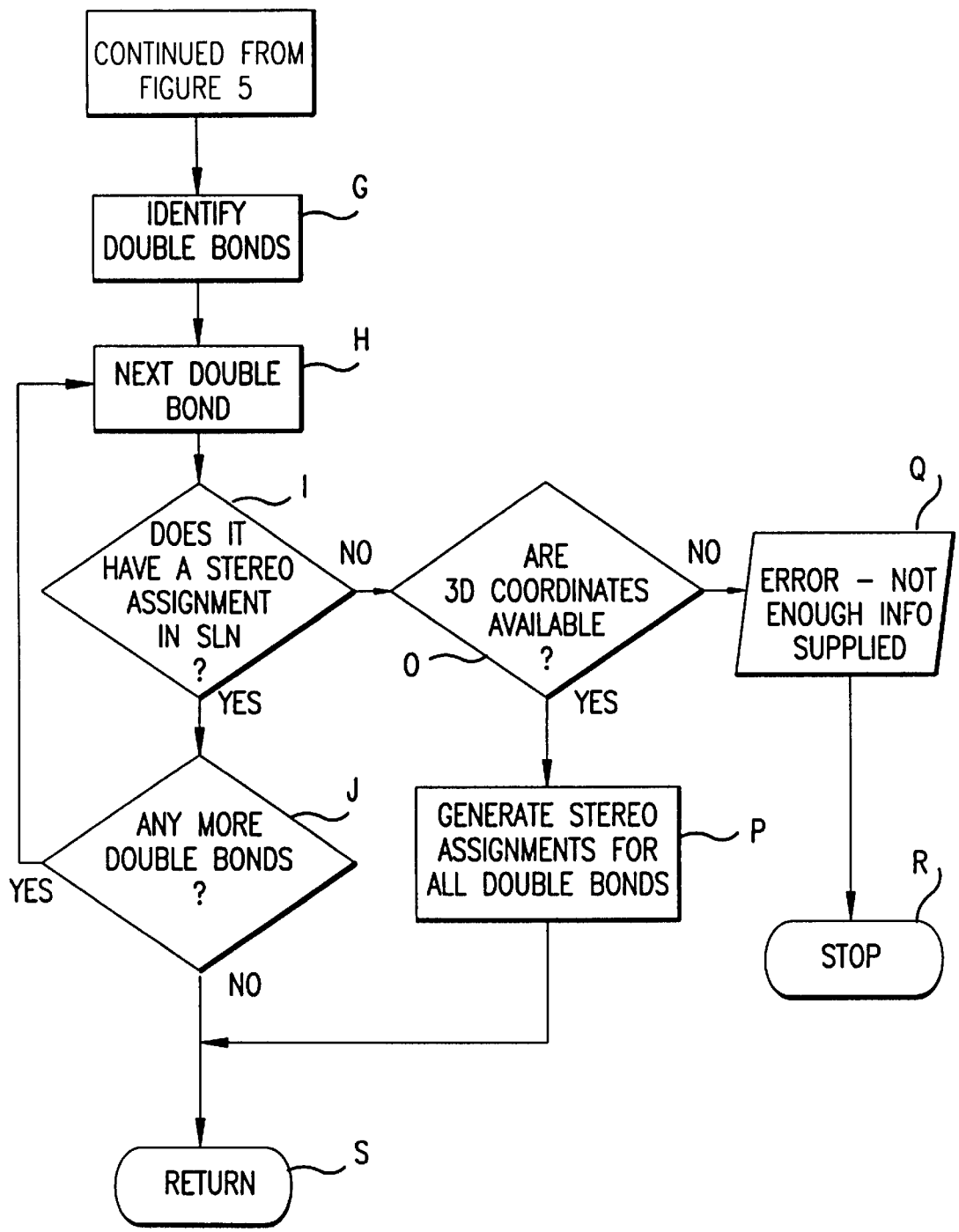

The several considerations which go into determining the fragments are shown in the flowchart of FIG. 4. At this point in the process the length of the fragments has already been determined (step "B" in FIG. 3), and the user of the method can specify whether atomic information, bond information, or connection information is to be used to specify the fragments. More specifically, the fragment specified in step "B" of FIG. 3 is obtained at "A" and tested at "B" to determine whether atom type information is to be ignored. If atomic information is to be ignored, all atom types in the fragment are changed to carbon, and whether to also ignore bond information is tested next at "C". If atomic information is not to be ignored at "B", whether to ignore bond information is tested at "C" directly. If bond information is to be ignored, all bonds in the fragment are changed to single bonds and whether to also use connection information is tested next at "D". If bond information is not to be ignored at "C", whether to use connection information is tested at "D" directly. If connection information is to be used, at "G" a place holding atom X is added to each fragment for each atom in the molecule which is connected to the fragment and the process returns at "H". If connection information is not to be used, the process returns directly.

As mentioned earlier, another significant advance of the method of this invention is the ability to take chirality of molecular fragments into account in construction a MOLECULAR HOLOGRAM. For this purpose it is necessary to identify all chiral centers and to verify that the SLN fragment representation contains the necessary chiral information. More specifically, in FIGS. 5 and 6, at "A" all tetrahedral centers in the molecule are identified. At "B" a tetrahedral center is specified and tested at "C" to determine whether it is chiral. If it is not chiral, At "K" the SLN stereochemistry attribute of N is assigned to it. If the molecule is chiral, it is tested at "D" to determine whether the center has a chiral assignment in the SLN representation. If the associated SLN does have the chiral assignment for the center, at "L" a check is made to determine whether any more tetrahedral centers need to be evaluated, and, if they do, the process loops to "B" and repeats itself.

If at "D" the center does not have a chiral assignment in the SLN, a check is performed at "E" to determine whether 3D coordinates are available for the center. If the 3D coordinates are not available, and error message is output at "M" and the entire process is stopped at "N" since the user set a chirality flag as input but did not provide sufficient 3D coordinate information to complete the analysis. If 3D coordinates were available, at "F" the stereo assignments for all chiral centers are generated. This may entail regenerating the stereo assignments for centers for which previous assignments existed, but is performed again to guarantee consistency amongst all 3D coordinates. Once the stereo assignments re made, a check is performed at "L" to confirm whether all tetrahedral centers have been examined, and, if they have not, the process loops back to "B" as noted above.

Once the tetrahedral centers have been evaluated, it is necessary to consider the stereochemistry resulting from double bonds which may be present. At "G" all double bonds are identified, a double bond is specified at "H", and tested at "I" to determine whether the associated SLN includes a stereo assignment. If the bond does have a stereo assignment, the test at "J" determines whether any more double bonds need to be considered, and, if there are more, the process loops back to "H" and is repeated. If no more double bonds need to be considered, the process returns at "S". If a double bond does not have a stereo assignment at "I", a check is made at "O" to determine whether 3D coordinates are available. If 3D coordinates are not available, an error message is printed out at "Q" and the entire process stopped at "R" since again the user set a chirality flag as input but did not provide sufficient 3D coordinate information to complete the analysis. If 3D coordinate information is available, at "P" the stereo assignments for all double bonds are generated. As above, this may entail regenerating the stereo assignments for double bonds for which previous assignments existed, but is performed again to guarantee consistency amongst all 3D coordinates. After stereo generation at "P", the process returns at "S".

Once the optimum HQSAR has been identified, the information can be used in several ways. For instance, individual molecules or those of an entire data base of molecules may be examined for likely activity in the same chemical system as the original molecules were measured. A MOLECULAR HOLOGRAM can be quickly calculated for each molecule or member of the data base using the values of M, N, and L which are associated with the optimal HQSAR and the PLS coefficients used with the MOLECULAR HOLOGRAM (by multiplying each hologram term by its associated PLS coefficient) to determine a likely value for the chemical activity of such molecule. This ability to quickly scan large data bases for molecules likely (based on the HQSAR) to have similar activities is a capability uniquely enabled by this invention.

Figure 7:
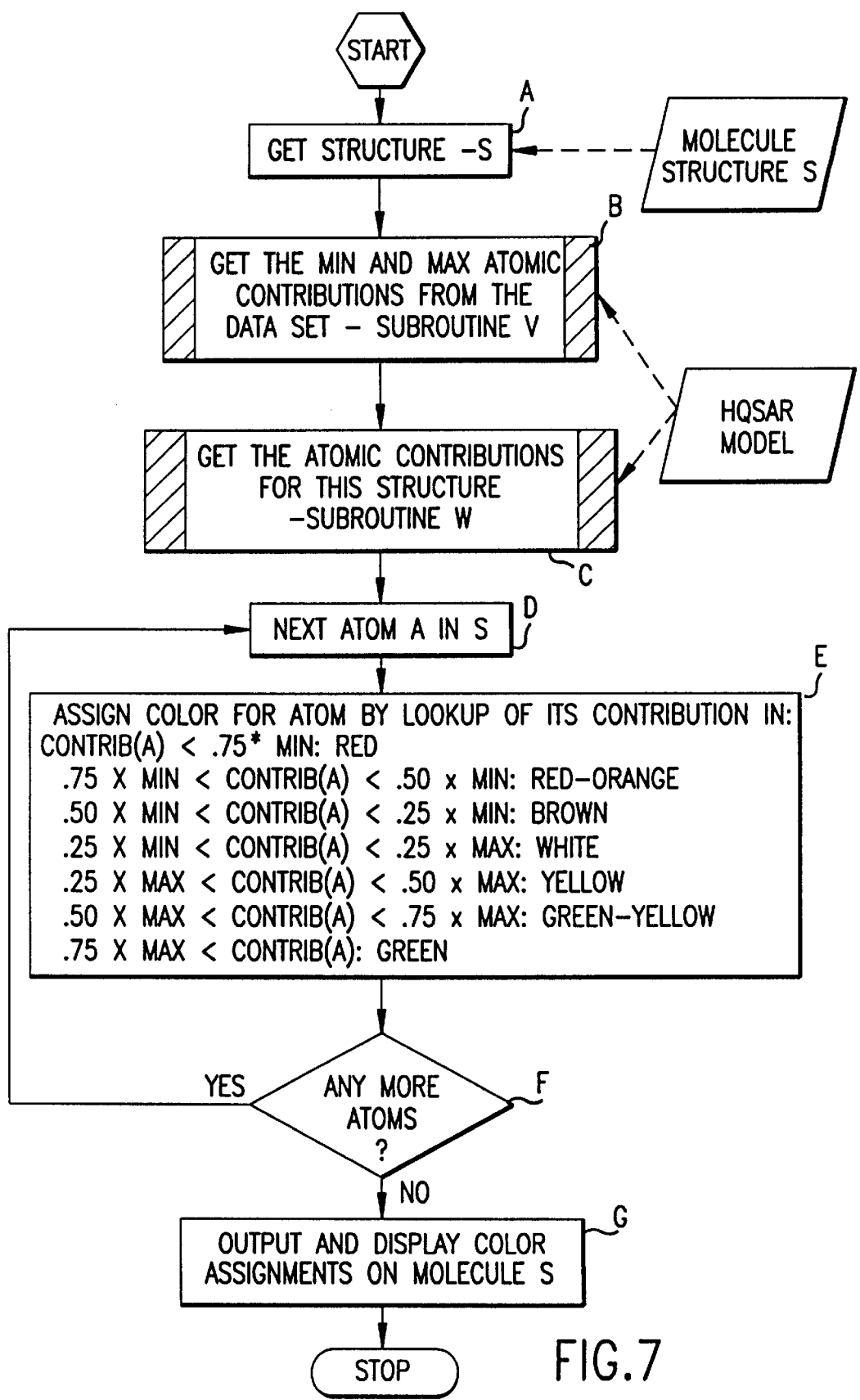
FIG. 7 is a flowchart showing the process of assigning color coding to atoms in each molecule.
Figure 8:
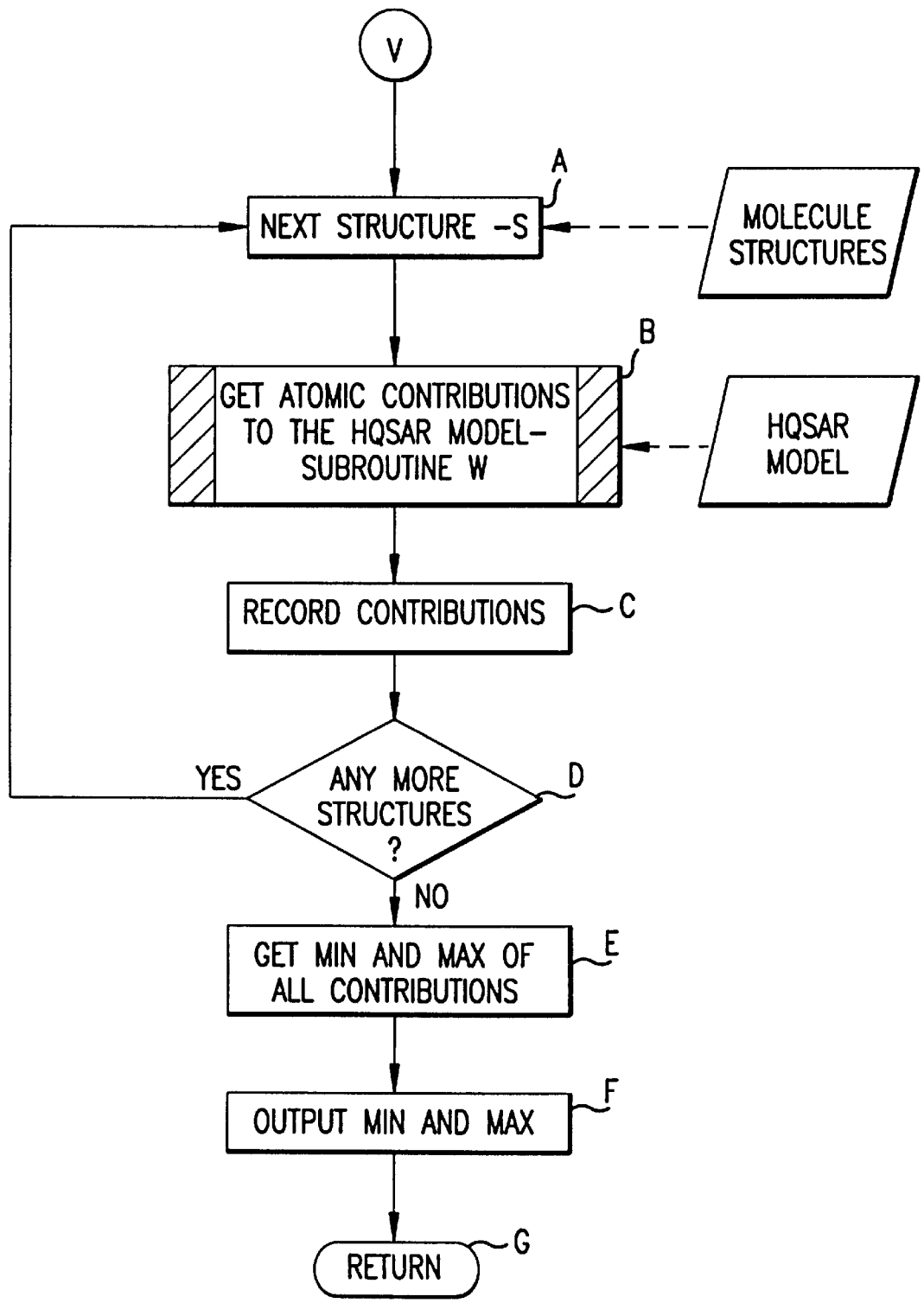
FIG. 8 is a flowchart showing the derivation of the weighting ranges used to determine the color coding of atoms.
Figure 9:
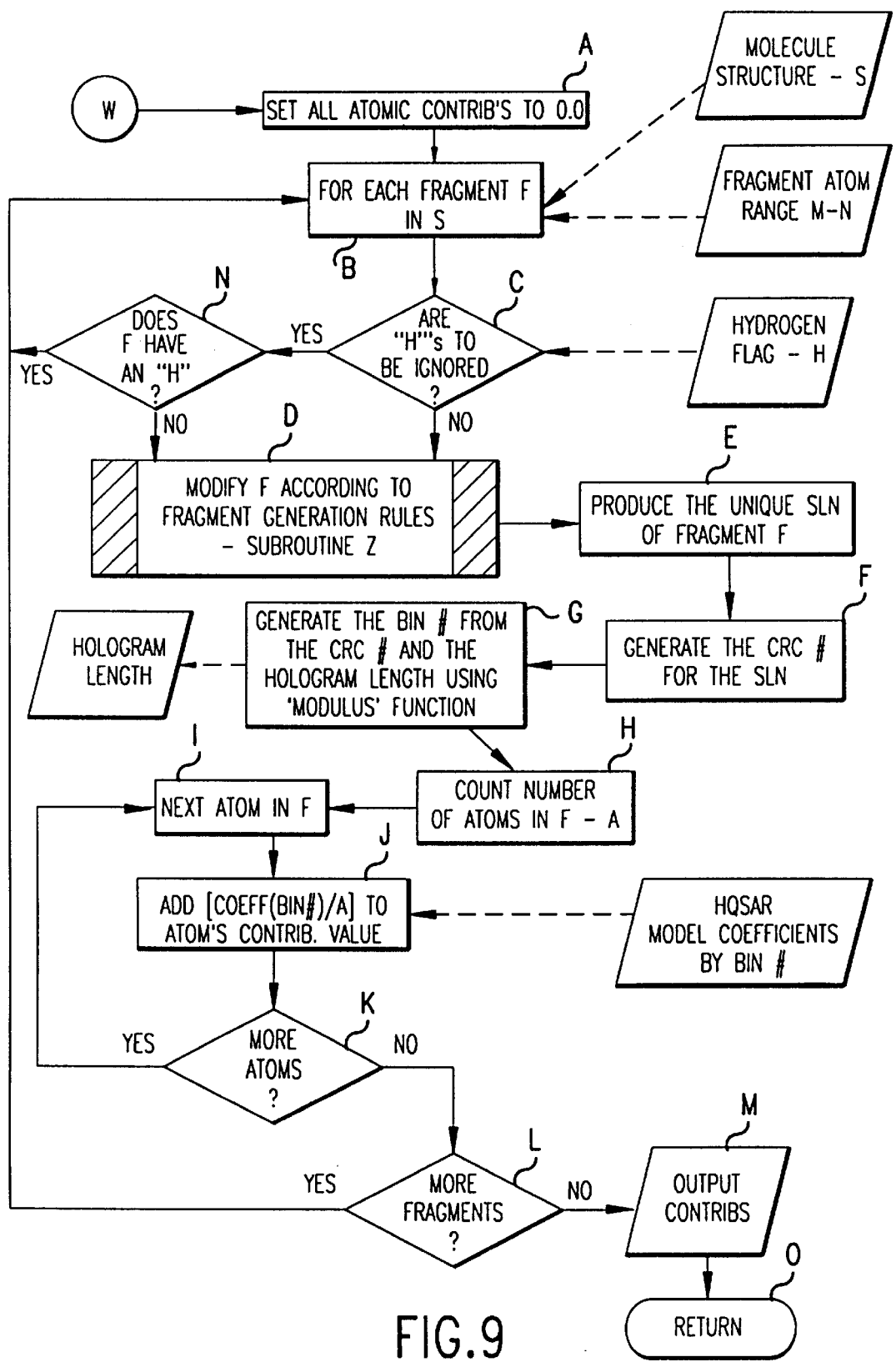
FIG. 9 is a flowchart showing the derivation of the weighting to be assigned to each atom for color coding.

Another manner of using the information derived by the invention is to examine the individual molecules which made up the test data set to see which of the atoms (atomic positions) in each molecule contributed most strongly (positively or negatively) to the identified structure-activity relationship. Such an understanding provides a medicinal chemist with knowledge of the likely sites of interaction of the molecule as well as with information on atoms or atomic positions which may be modified to achieve even greater activity. FIGS. 7, 8, and 9 illustrate how this is accomplished.

The overall process is shown in the flowchart of FIG. 7. However, before considering the flowchart of FIGS. 7 and 8, the flowchart of FIG. 9 will be discussed since the individual atomic weightings are central. The basic problem which this part of the method of the invention solves is how to use the PLS derived structure-activity coefficients to show the extent of the contribution of each atom to the structure-activity relationship. Since each bin or position in the MOLECULAR HOLOGRAM of a molecule is associated with a PLS derived coefficient, all atoms comprising all fragments which were hashed to that bin are considered to have contributed equally to the coefficient since there is no way to know which, amongst the atoms making up the fragments, was most or least responsible for the structure-activity relationship. Thus a weighting value for each atom is derived by dividing the PLS coefficient (a positive or negative value) by the number of atoms in the fragments assigned to that position. When this is done for each position in the fingerprint, individual atoms will have received weights from many different fingerprint positions since individual atoms typically are found in several fragments.

The process is shown in the flowchart of FIG. 9 as Subroutine W. The method of determining atomic weightings begins by following substantially the same pattern as already seen in FIG. 3 for generating MOLECULAR HOLOGRAMS. After setting all atomic contributions to O at "A" the process proceeds from "B" through "G" to generate the fragment SLN and find the position or bin to which the fragment was assigned. Then, at "H" the total number of atoms in the fragment is counted and an atom specified at "I". At "J", for each atom in the fragment a weight is assigned equal to the coefficient of the bin divided by the number of atoms in the fragment. A check is performed at "K" to determine whether any more atoms need to be weighted, and, if there are more, the process lops back to "I" and is repeated. If test "K" determines that all atoms have been weighted, a check is made at "L" to determine whether there are any more fragments to consider, and, if there are, the process loops back to "B". If the test at "L" indicates that all fragments have been considered, the atomic weightings are output at "M" and the process returns at "O".

Across the whole set of molecules in the data set, a minimum atomic weighting and a maximum atomic weighting can be determined. The minimum and maximum weightings may or may not be found associated with the same molecule in the data set. Therefore, before assigning colors to all the atoms across the data set to indicate their relative contributions to the structure-activity analysis, it is necessary to establish the range—the minimum and maximum values of the weightings. More specifically, the flowchart shown in FIG. 8 describes this process. A molecule is specified at "A" and the weightings for each atom in the molecule is obtained at "B" from Subroutine W discussed above. These values are stored at "C", and at "D" a check is performed to determine whether weighting for atoms in any more molecules need to be obtained. If there are more molecules, the process loops back to "A" and the process is repeated. Once all molecules have been considered, the Minimum and Maximum weightings are determined at "E", output at "F", and the process returns at "G"

For each atom in the molecule a color is assigned based on the minimum and maximum weighting values across the data set of molecules. The coloring procedure is shown in the flowchart of FIG. 7. For each molecule specified at "A" the minimum and maximum weightings found in the data set of which that molecule is a member are obtained at "B" from Subroutine V as discussed above. The individual weightings for each atom in the molecule are then obtained at "C" from Subroutine W discussed above. For each atom in the molecule specified at "D", a color is assigned based on the atom's weighting according to the scale at "E". A check is performed at "F" to determine whether any more atoms need to be considered, and if there are, the process loops back to "D". Once all atoms in a molecule have been colored, the molecular structure is graphically displayed at "G". The colors and the groupings of atoms of different colors immediately indicate which atoms were most or least associated with the derived structure-activity relation ship.

5. Advancements achieved by the invention.

A key component of this process when used with PLS is the internal statistical validation of the models generated using the technique of leave-one-out cross-validation. Cross-validated $r^2$ and standard error of estimate values are used when using PLS, and classification success rates are used when using classification analysis. In each case, the statistical measures are associated with the parameters L, M, and N used to generate the corresponding MOLECULAR HOLOGRAM.

This process determines the optimal (statistically most significant) set of parameters to use in hologram generation such that the resultant hologram yields the optimal validated QSAR model. Such a process of validated QSAR model generation has not hitherto been possible, and this process affords huge benefits to the user and extends the scope of QSAR modeling to a much wider audience than is applicable to techniques such as CoMFA or Apex-3D.

This invention using molecular holograms extends far beyond the concept of merely comparing 2D fingerprints in pairwise fashion as is common in the prior art. It has been shown that powerful chemometric techniques, including PLS and discriminant analysis, can be applied to molecular holograms to yield predictive quantitative structure-activity models. Further, the application of the chemometric techniques to the traditional 2D fingerprints described above does not, in general, produce high quality quantitative structure-activity models. In addition, no other QSAR method takes either chirality or the frequency of fragment occurrence into account. No other QSAR method allows parameter adjustment so as to determine the set of parameters to use if generation of an optimal, statistically validated QSAR model is the goal, All other approaches, like CoMFA, force the user to make an arbitrary choice of input parameters and either succeed or fail accordingly. MOLECULAR HOLOGRAM QSAR examines a large set of parameter combinations to find the best set, before it succeeds or fails.

REFERENCES

1. U.S. Pat. No. 5,025,388, European Patent No. 0592421
2. Willett, P.; Winterman, V.; Bawden, D. Implementation of Nonhierarchic Cluster Analysis Methods in Chemical Information Systems: Selection of Compounds for Biological Testing and Clustering of Substructure Search Output, *J. Chem. Inf. Comput. Sci.* 1986, 26, 109–118
3. Blankley, C. J. et al, Stigmata: An Algorithm to Determine Structural Commonalities in Diverse Datasets, *J. Chem. Inf. Comput. Sci.* 1996, 34, 862–871
4. MACCS-II; MDL Ltd.: San Leandro, Calif., 1992

5. James, C. A., Weininger, D. *Daylight Theory Manual*; Daylight Chemical Information Systems, Inc.: 1995

6. Wold, S., Abano, C., Dunn, W. J. III, et al., Multivariate Data Analysis in Chemistry, in CHEMOMETRICS: *Mathematics and Statistics in Chemistry*, Kowalski, B., Reidel, Dordrecht, Netherlands (1984)

We claim:

1. A computer-based method of generating an optimal quantitative structure-activity relationship among a series of molecules comprising the steps of:
   (a) defining a list of values for hologram length and fragment size range;
   (b) selecting a value from said list for length L;
   (c) selecting values from said list for fragment size in a range M to N;
   (d) using the selected values of M and N, defining a MOLECULAR HOLOGRAM molecular structural descriptor for each molecule in the series wherein each molecule is associated with an activity value;
   (e) correlating the MOLECULAR HOLOGRAM molecular structural descriptor and activity value of each molecule with all the other molecules in said series to obtain a structure-activity relationship;
   (f) repeating steps (b) through (e) for all values of L on the list;
   (g) selecting the optimal structure-activity relationship based on the statistical correlation values; and
   (h) outputting for the selected optimal structure-activity relationship the values of L, M, and N, used for MOLECULAR HOLOGRAM generation along with associated measures of statistical significance.

2. The method of claim 1 comprising the following additional step after step (h) of:
   (i) weighting each atom in each molecule by its contribution to the structure-activity relationship.

3. The method of claim 2 in which the weighting of each atom is displayed by visually perceivable indicia.

4. The method of claim 3 in which the visually perceivable indicia is pseudocoloring.

5. A computer-based method of generating an optimal quantitative structure-activity relationship among a series of molecules comprising the steps of:
   (a) defining a list of values for hologram length and fragment size range;
   (b) generating a MOLECULAR HOLOGRAM for each molecule for each fragment size range and for each hologram length;
   (c) correlating the MOLECULAR HOLOGRAMs to determine for each fragment size range and hologram length a structure-activity relationship for the series of molecules along with associated measures of statistical significance;
   (d) selecting as the optimal structure-activity relationship the relationship with the greatest statistical significance.

6. The method of claim 5 comprising the following additional step after step (h) of:
   (i) weighting each atom in each molecule by its contribution to the structure-activity relationship.

7. The method of claim 6 in which the weighting of each atom is displayed by visually perceivable indicia.

8. The method of claim 7 in which the visually perceivable indicia is pseudocoloring.

9. A computer based method of representing the structure of a molecule as a weighted 2D fingerprint of length L of fragments having a minimum size M and a maximum size N comprising the steps of:
   (a) generating a list of all fragments found in the molecule having a minimum size M and a maximum size N including branched and cyclic fragments;
   (b) producing a unique representation of each fragment;
   (c) generating for each unique representation of each fragment a pseudo-random number which will always be generated for that fragment;
   (d) assigning each fragment to a specific position in the fingerprint using the operator "modulus" with the length L and the pseudo-random number; and
   (e) incrementing the value stored at each assigned fragment position for each occurrence of each fragment in the molecule assigned to that position.

10. A weighted 2D fingerprint of a molecule generated by the following method:
    (a) generating a list of all fragments found in the molecule having a minimum size M and a maximum size N including branched and cyclic fragments;
    (b) producing a unique representation of each fragment;
    (c) generating for each unique representation of each fragment a pseudo-random number which will always be generated for that fragment;
    (d) assigning each fragment to a specific position in the fingerprint using the operator "modulus" with the length L and the pseudo-random number; and
    (e) incrementing the value stored at each assigned fragment position for each occurrence of each fragment in the molecule assigned to that position.

11. A computer based method of representing the structure of a molecule including any chiral centers as a weighted 2D fingerprint of length L of fragments having a minimum size M and a maximum size N comprising the steps of:
    (a) identifying all tetrahedral centers in the molecule;
    (b) determining which tetrahedral centers are chiral;
    (c) generating stereo assignments for all chiral centers;
    (d) generating a list of all fragments found in the molecule having a minimum size M and a maximum size N including branched and cyclic fragments;
    (e) producing a unique representation of each fragment;
    (f) generating for each unique representation of each fragment a pseudo-random number which will always be generated for that fragment;
    (g) assigning each fragment to a specific position in the fingerprint using the operator "modulus" with the length L and the pseudo-random number; and
    (h) incrementing the value stored at each assigned fragment position for each occurrence of each fragment in the molecule assigned to that position.

12. A weighted 2D fingerprint of a molecule containing chiral centers generated by the following method:
    (a) identifying all tetrahedral centers in the molecule;
    (b) determining which tetrahedral centers are chiral;
    (c) generating stereo assignments for all chiral centers;
    (d) generating a list of all fragments found in the molecule having a minimum size M and a maximum size N including branched and cyclic fragments;
    (e) producing a unique representation of each fragment;
    (f) generating for each unique representation of each fragment a pseudo-random number which will always be generated for that fragment;
    (g) assigning each fragment to a specific position in the fingerprint using the operator "modulus" with the length L and the pseudo-random number; and
    (h) incrementing the value stored at each assigned fragment position for each occurrence of each fragment in the molecule assigned to that position.

13. A computer based method of representing the structure of a molecule including any connectivity relationships as a weighted 2D fingerprint of length L of fragments having a minimum size M and a maximum size N comprising the steps of:
   (a) generating a list of all fragments found in the molecule having a minimum size M and a maximum size N including branched and cyclic fragments;
   (b) identifying all positions in each fragment at which the fragment is connected to the molecule;
   (c) adding a placeholder atom to each fragment for each atom in the molecule connected to the fragment;
   (d) producing a unique representation of each fragment;
   (e) generating for each unique representation of each fragment a pseudo-random number which will always be generated for that fragment;
   (f) assigning each fragment to a specific position in the fingerprint using the operator "modulus" with the length L and the pseudo-random number; and
   (g) incrementing the value stored at each assigned fragment position for each occurrence of each fragment in the molecule assigned to that position.

14. A weighted 2D fingerprint of a molecule containing including connectivity relationships generated by the following method:
   (a) generating a list of all fragments found in the molecule having a minimum size M and a maximum size N including branched and cyclic fragments;
   (b) identifying all positions in each fragment at which the fragment is connected to the molecule;
   (c) adding a placeholder atom to each fragment for each atom in the molecule connected to the fragment;
   (d) producing a unique representation of each fragment;
   (e) generating for each unique representation of each fragment a pseudo-random number which will always be generated for that fragment;
   (f) assigning each fragment to a specific position in the fingerprint using the operator "modulus" with the length L and the pseudo-random number; and
   (g) incrementing the value stored at each assigned fragment position for each occurrence of each fragment in the molecule assigned to that position.

15. A computer based method of representing the structure of a molecule including any chiral centers and connectivity relationships as a weighted 2D fingerprint of length L of fragments having a minimum size M and a maximum size N comprising the steps of:
   (a) identifying all tetrahedral centers in the molecule;
   (b) determining which tetrahedral centers are chiral;
   (c) generating stereo assignments for all chiral centers;
   (d) generating a list of all fragments found in the molecule having a minimum size M and a maximum size N including branched and cyclic fragments;
   (e) identifying all positions in each fragment at which the fragment is connected to the molecule;
   (f) adding a placeholder atom to each fragment for each atom in the molecule connected to the fragment;
   (g) producing a unique representation of each fragment;
   (h) generating for each unique representation of each fragment a pseudo-random number which will always be generated for that fragment;
   (i) assigning each fragment to a specific position in the fingerprint using the operator "modulus" with the length L and the pseudo-random number; and
   (j) incrementing the value stored at each assigned fragment position for each occurrence of each fragment in the molecule assigned to that position.

16. A weighted 2D fingerprint of a molecule containing chiral centers and reflecting connectivity relationships generated by the following method:
   (a) identifying all tetrahedral centers in the molecule;
   (b) determining which tetrahedral centers are chiral;
   (c) generating stereo assignments for all chiral centers;
   (d) generating a list of all fragments found in the molecule having a minimum size M and a maximum size N including branched and cyclic fragments;
   (e) identifying all positions in each fragment at which the fragment is connected to the molecule;
   (f) adding a placeholder atom to each fragment for each atom in the molecule connected to the fragment;
   (g) producing a unique representation of each fragment;
   (h) generating for each unique representation of each fragment a pseudo-random number which will always be generated for that fragment;
   (i) assigning each fragment to a specific position in the fingerprint using the operator "modulus" with the length L and the pseudo-random number; and
   (j) incrementing the value stored at each assigned fragment position for each occurrence of each fragment in the molecule assigned to that position.

17. Predicting, based on a HQSAR, the likely activity of a molecule in the same system in which the activities of a test data set of molecules was determined by:
   (a) constructing the MOLECULAR HOLOGRAM of the molecule using the values of L, M, and N used to determine the optimal HQSAR; and
   (b) applying the coefficients determined by the optimal HQSAR for each position of the MOLECULAR HOLOGRAM to the MOLECULAR HOLOGRAM of the molecule to generate a predicted activity for that molecule.

18. A computer based method for selecting from a data base of molecules those molecules most likely to have an activity similar to the activity possessed by a series of molecules for which an optimal HQSAR has been generated comprising the following steps:
   (a) generating for each molecule in the data base a MOLECULAR HOLOGRAM using the values of L, M, and N associated with the optimal HQSAR;
   (b) applying the coefficients determined by the optimal HQSAR for each position of the MOLECULAR HOLOGRAM to the MOLECULAR HOLOGRAM of the each molecule in the data base to generate a predicted activity for each molecule;
   (c) selecting those molecules in the data base whose predicted activities fall within a predetermined range of similarity.

19. A group of molecules selected from a data base having activities similar to the activity possessed by a series of molecules for which an optimal HQSAR has been generated by the following steps:
   (a) generating for each molecule in the data base a MOLECULAR HOLOGRAM using the values of L, M, and N associated with the optimal HQSAR;
   (b) applying the coefficients determined by the optimal HQSAR for each position of the MOLECULAR HOLOGRAM to the MOLECULAR HOLOGRAM of the each molecule in the data base to generate a predicted activity for each molecule;
   (c) selecting those molecules in the data base whose predicted activities fall within a predetermined range of similarity.

* * * * *